United States Patent [19]

Lieutaud et al.

[11] Patent Number: 4,979,196

[45] Date of Patent: Dec. 18, 1990

[54] MAMMOGRAPH

[75] Inventors: Olivier Lieutaud, Larmolaye; Alain Marie, Clamart, both of France

[73] Assignee: General Electric CGR S.A., Issy Les Moulineaux, France

[21] Appl. No.: 318,836

[22] Filed: Mar. 6, 1989

[30] Foreign Application Priority Data

Mar. 8, 1988 [FR] France .................. 88 02916

[51] Int. Cl.⁵ .............................. A61B 6/04
[52] U.S. Cl. ..................... 378/37; 378/195; 378/196
[58] Field of Search ............. 378/37, 195–198

[56] References Cited

U.S. PATENT DOCUMENTS

| 3,824,397 | 7/1974 | Bauer et al. | |
|---|---|---|---|
| 4,613,982 | 9/1986 | Dornheim et al. | 378/37 |
| 4,649,560 | 3/1987 | Grady et al. | 378/196 |
| 4,741,015 | 4/1988 | Charrier | 378/196 |
| 4,926,453 | 5/1990 | Toniolo | 378/37 |

FOREIGN PATENT DOCUMENTS

| 0229971 | 7/1987 | European Pat. Off. |
| 973092 | 12/1959 | Fed. Rep. of Germany |
| 3321057 | 12/1984 | Fed. Rep. of Germany |
| 2363316 | 3/1978 | France |

Primary Examiner—Carolyn E. Fields
Assistant Examiner—David P. Porta
Attorney, Agent, or Firm—Oblon, Spivak, McClelland, Maier & Neustadt

[57] ABSTRACT

A mammograph is made, wherein the X-ray tube and the work top are held facing each other by a stirrup, making it easy for an X-ray technician to reach the breast to be X-rayed. The stirrup is shaped like a ring and can rotate on itself in sliding on a complementary ring, so as to reduce the inertia of the movable masses, to bring about radiography under oblique or even horizontal incidence. Furthermore, the structure is preferably moved away from a control cabinet for the mammograph, to enable an X-ray technician to come between this cabinet and the patient so as to facilitate preparations for taking a picture.

7 Claims, 2 Drawing Sheets

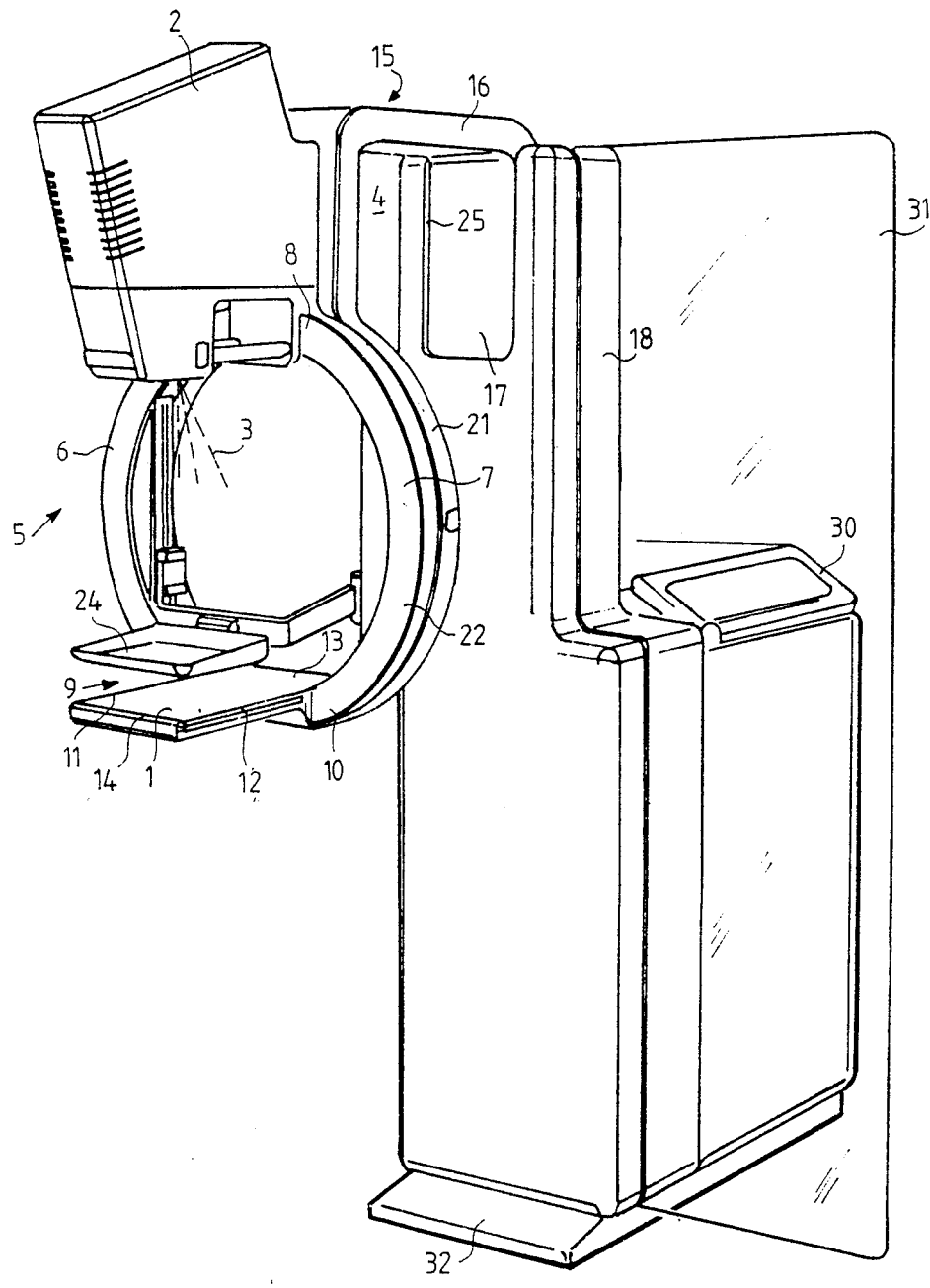

FIG_2
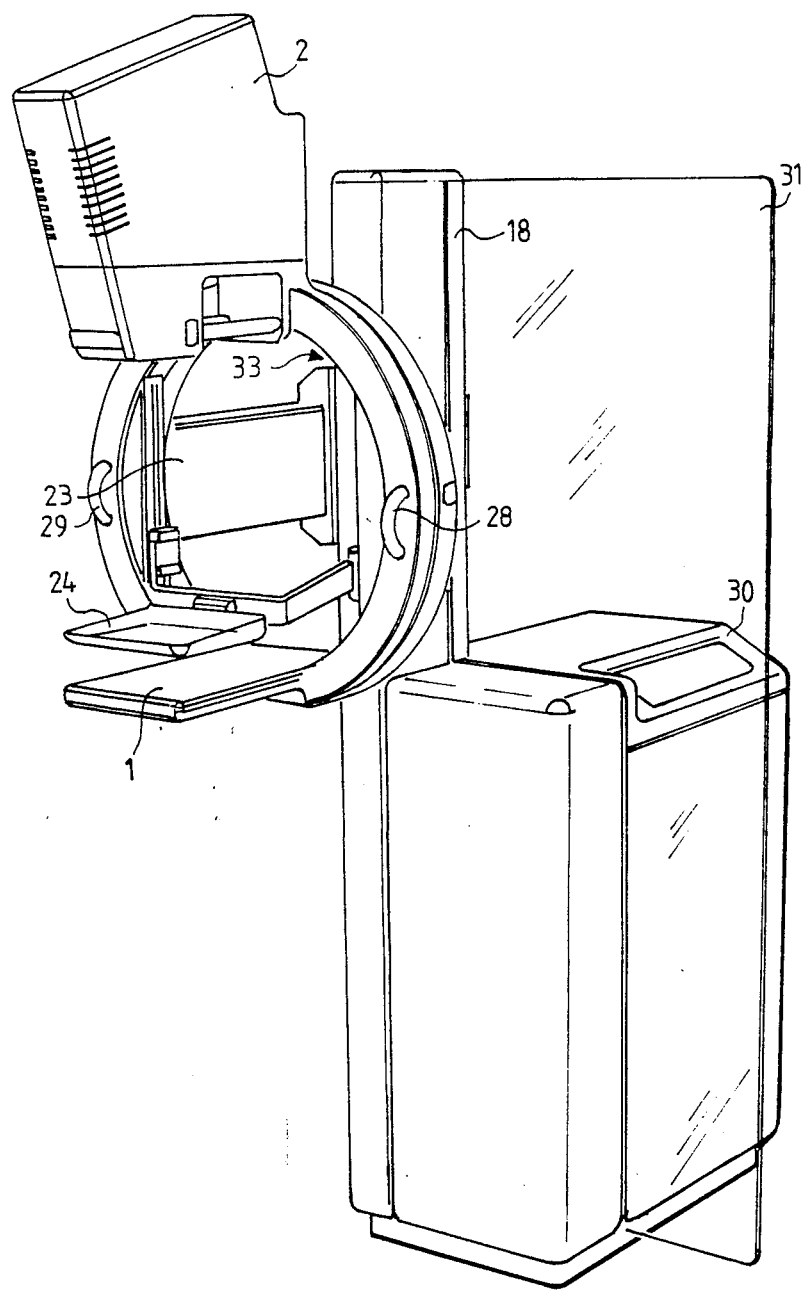

MAMMOGRAPH

BACKGROUND OF THE INVENTION

1. Field of the Invention

An object of the present invention is a mammograph which can be used in radiology and, more particularly, in medicine. A mammograph is an instrument designed to give an image of the tissue structures of a breast of a patient under examination. The invention is aimed at making it easier for X-ray technicians to operate instruments of this type, and, therefore, at increasing the comfort of a patient undergoing an X-ray examination of the breast with an instrument of this type.

2. Description of the Prior Art

A mammograph essentially comprise an X-ray tube and a work top. The radiation of X-rays from the tube is directed towards the work top, most often in a direction that is substantially perpendicular to this top. The work top has a surface designed to receive and support the breast to be X-rayed. Downstream from this surface with respect to the radiation, a housing is made beneath this top. It is designed to receive a cassette with a radiosensitive film to give an account of the X-ray examination. Possibly, a supporting plate, or pelote, transparent to X-radiation, is interposed between the focus of the tube and the work top in order to compress the breast being examined at the instant when the picture is taken. Because of this compression, the supporting plate is further provided with devices to relax the pressure as soon as the picture has been taken. The setting of a mammograph for the distance between the focus of the X-ray tube (in fact the X-ray tube itself) and the surface of the work top is defined in the factory. In principle, this distance is fixed. To be able to take differences in height among patients into account, these two fittings are mounted fixedly, in a jutting out position, on a post. The post can then be raised or brought down with respect to a mean position to take this difference in the height of patients into account. Furthermore, for certain examinations, the breast to be X-rayed has to be irradiated laterally. Hence, the post which supports the X-ray tube and the work top is solidly joined to a horizontal shaft. This set can then rotate around this shaft. For example, the post is swung by a quarter turn around the shaft so as to obtain horizontal alignment of the tube and the work top.

In practice, these mammographs have many drawbacks. For, it is known that the alignment of the rotation shaft is substantially at mid-height of the distance between the focus of the X-ray tube and the work top. In practice, it may even be placed as close as possible to the work top itself, so that no corrections have to be made in the height of the device when the side shots are taken. Consequently, when these side shots are taken, the X-ray tube juts out with respect to the instrument in a twofold way. Firstly, it juts out towards the front of the instrument, towards the front of the post as observed earlier. Secondly, it now also protrudes with respect to the shaft. Now, the X-ray tube with its control and insulation equipment is heavy. It naturally causes the shaft to rotate and the post to swing. To avoid having to install brakes to restrict the swinging of the post when the tube is in a position for taking lateral pictures, the common practice is to place a counterweight at the end of the post, in a position that is substantially symmetrical with the X-ray tube with respect to the shaft. This counterweight has two drawbacks.

Firstly, it is bulky. For, since it is raised when the side shots are taken, it hampers the movement of the X-ray technician. Secondly, it helps make it difficult to manipulate the X-ray tube/work top unit when changing the incidence. For, the inertia of a device of this type is great. Since the unit is manipulated by hand, this inertia is too great to enable high working rates, namely to enable a large number of patients to be put before the instrument in a given period.

Furthermore, the X-ray examination of a breast can also be done with the injection of a contrast medium. For example, a product that is opaque to X-rays is injected through the nipple into the milk ducts, just when the shot is taken. The presence of the post, located directly before the breast, hampers this maneuver and is, at the same time, also troublesome for the patient. During this delicate operation, the patient may seek to make visual contact with the X-ray technician, which she cannot do because of the post which is between them.

Besides, there are other known upholding structures where the post is replaced by a stirrup suspended from the ceiling. The X-ray tube is held at the top of the stirrup. The work top is hooked, by its two side edges, to the ends of the legs of the stirrup. In this case, it is easy to reach the patient. But then, the handling of the suspension to bring the patient into positions corresponding to lateral or oblique incidence can only be motor driven. Consequently, it is slow, and the equipment itself is costly.

An object of the invention is to overcome these drawbacks by proposing a structure to hold, respectively, the X-ray tube and the work top, a structure which is better suited to being manipulated when changing incidence and enables satisfactory technical and psychological contact between the patient and the X-ray technician. In substance, the invention provides for replacing the stirrup by a ring. The X-ray tube is hooked to the top of the ring. Ends of arcs of the ring are then fixed laterally to the work top. The result thereof is that, in the arch which is formed within this circular stirrup and which somewhat overhangs the work top, it now becomes possible to reach the patient's breast while she can see the X-ray technician. Furthermore, it becomes far easier to manipulate the tube, the fixing point of which slides on the rim of the ring. It is easier to change incidence without coming up against great inertia. There is no longer any troublesome counterweight. Finally, the ring can be fixed to a post or to a rest which is vertically movable so as to be adaptable to the patient's height.

To make the X-ray technician's work even easier, the circular stirrup is suspended from a bracket which moves this unit away from the post. The X-ray technician can then stand below this bracket, between the patient and the cabinet containing all the instruments control elements.

SUMMARY OF THE INVENTION

An object of the invention, therefore, is a mammograph comprising a work top, an X-ray tube oriented towards this work top and a structure for holding the X-ray tube with respect to the work top, said structure comprising a stirrup, firstly to hold the X-ray tube and, secondly, to hold the side edges of the work top by the ends of the legs of the stirrup, said stirrup having the general shape of a ring and comprising, in order to receive the tube in a circular sliding motion with respect to the work top, a holding ring to hold the work top which can slide in a fixing ring to hold the tube.

BRIEF DESCRIPTION OF THE DRAWINGS

The invention will be better understood from the following description and the accompanying figures. These figures are given purely by way of indication and in no way restrict the scope of the invention.

Of these figures:

FIG. 1 shows a mammograph provided with a circular stirrup according to the invention;

FIG. 2 shows an alternative to the previous embodiment, wherein a bracket is replaced by a side rest.

DESCRIPTION OF PREFERRED EMBODIMENTS

FIG. 1 shows a mammograph having a work top 1 and an X-ray tube 2, the X-radiation 3 of which is oriented towards the work top 1. A structure 4 is used to keep the work top 1 and the X-ray tube 2 fixed with respect to each other. This fixing is set in the factory. The structure 4 essentially has a circular stirrup 5 provided with legs, or arcs of rings, 6 and 7 respectively, and a top 8. The X-ray tube is fixed to the top 8 of the stirrup. The ends 9 and 10, respectively, of the legs 6 and 7 are fixed to the corresponding side edges, 11 and 12 respectively, of the work top 1. In one example, the surface of the work top is substantially rectangular, and the ends 9 and 10 of the legs 6 and 7 are fixed to the edges 11 and 12 of the work top, near an edge 13 of this plane, the edge 13 itself being opposite an edge 14 against which the patient leans. The work top 1 is transparent to X-radiation. On the edges 11 and 12, it has slide ways to fix a cassette, not shown, with a radiosensitive film.

The structure 4 also has a bracket 15, from the tip of which the top 8 of the circular stirrup 5 is suspended in a solidly joined way. This stirrup 5 has a projecting beam 16 and a post 17. The length of the beam 16 makes it possible to move the stirrup 5, along with all the equipment that it supports, away from a control cabinet 18. The gap created then enables the X-ray technician to come between the cabinet 18 and the stirrup 5 to position the breast to be X-rayed. Because of the gap which allows the X-ray technician to pass through, the weight of the cabinet 18 should be enough to prevent the entire mammograph from tipping forward.

To enable oblique or even horizontal incidence, the stirrup now has a circular shape and is formed by at least two rings. A first ring 21 is, for example, solidly joined to the bracket 15 while a second ring 22 may support, firstly, the X-ray tube 2 and, secondly, the work top. The rings 21 and 22 can rotate with respect to each other as with the two rings of a ball bearing. In one example, each ring has a slide way, the profile of which complements that of the other slide way or that of a third intermediate ring, between these two rings, so that they clutch each another and so that they can no longer permit any relative motion other than rotations on their common axis of rotation.

This axis of rotation of the rings is placed substantially at mid-height between the center of gravity of the X-ray tube and the supporting surface of the work top. To avoid having to make major height adjustments when changing incidence, the surface of the work top could be placed, to a substantially small extent, beneath the alignment of this axis of rotation. It would suffice to raise, accordingly, the fastening of the work top 1 with reference to the center of rotation of the ring. Should it become necessary, the work top could also be shifted slightly towards the bottom of the ring. The solution given by the invention provides notable improvement as compared with the prior art, inasmuch as the inertia offered when changing incidence is reduced to the inertia resulting from the mass of the X-ray tube, the mass of the work top and the mass of the stirrup without it's being any longer necessary to take into account the masses of a swinging post, beam masses counterweight masses. Nonetheless, the presence of the bracket 15 enables the X-ray technician, as previously, to take action easily, by coming between the cabinet and the patient 18.

FIG. 2 shows an alternative to the embodiment of FIG. 1, wherein the bracket, provided with its vertical post, is replaced by a substantially horizontal rest 23. The rest 23 supports one of the legs, for example the leg 6, of the stirrup 5. In this FIG. 2, the stirrup is also a circular stirrup, which also enables the reduction of the inertia when changing incidence. The rest 23 may be telescopic and may slide in a slide way 33 fixed to the cabinet 18.

To take differences in height among patients into account, the structure may, of course, move vertically. In FIG. 1, the post 17 moves vertically. In view of the weight, this movement should be motor driven. The shift of the post is often balanced by counterweights connected by chains and bearings to the post 19. The movement of the post is guided through friction by rollers in guides such as the sleeve 25. It is noted that the vertical movement of the structure 4 of FIG. 1 is simpler than the vertical movement of a shaft for the swinging of a post in the prior art. For, it is simpler to move a post longitudinally than to move a post and a rotational shaft. In practice, in view of the counterweight preventing the forward tipping of a mammograph, the rotation shaft should get driven in to a sufficient depth within the cabinet 18. During the vertical movement, this shaft sweeps a space bounded by the guides within this cabinet. This space cannot be occupied by the mammograph control instruments. The mammograph then has to be bigger. In certain hospitals where there are problems of space, the approach using the horizontal bracket of FIG. 2 becomes necessary. However, this approach restricts access by the X-ray technician to only one side of the space created between the patient and the control cabinet. By contrast, this less bulky version does not make it necessary to have a shoe 32 (FIG. 1) at the foot of the cabinet 18 to compensate for the jutting out of the tube/work top unit.

A supporting plate or tray 24 is used to compress the breast during an X-ray examination. Preferably, this supporting plate is also held by its side edges on the legs, 6 and 7 respectively, of the stirrup 5. The mechanism used to control the compression and loosening of this plate may be adjusted so as to simultaneously release both supports at the end of the shot. This mechanism is of a known type.

Finally, for its manipulation, the stirrup could be provided with side handles, such as the handles 28 and 29 of FIG. 2 for example. The mammograph is further provided with other standard means such as a control desk 30 or a pane 31 to protect the X-ray technicians.

The invention further provides another advantage. The work top can be kept fixed while the X-ray tube is made to rotate alone. In this case, this tube and the work top are not solidly joined to one and the same ring.

They are each solidly joined to a different ring. These rings can be held by a third ring, in a mutually imbricated way. It is then possible to achieve oblique incidence of a particular type. The conditions of the setting of the tube with respect to the work top could then be modified in the factory.

What is claimed is:

1. A mammography device comprising a work top, an X-ray tube oriented towards said work top and a structure for holding the X-ray tube with respect to the work top, said structure comprising a stirrup, firstly to hold the X-ray tube and, secondly, to hold the side edges of the work top by the ends of the legs of the stirrup, said stirrup having the general shape of a ring and comprising, in order to receive the tube in a circular sliding motion with respect to the work top, three rings, a first ring to hold the work top, said first ring being able to slide in a second ring, said second ring being designed to hold the tube, said first and second rings being held by a third ring in a mutually imbricated way.

2. A mammography device comprising a work top, an X-ray tube oriented towards said work top and a structure for holding the X-ray tube with respect to the work top, said structure comprising a stirrup, firstly to hold the X-ray tube and secondly to hold the side edges of the work top by the ends of the legs of the stirrup, said stirrup having the general shape of a ring and comprising a first ring to hold the work top and the tube, said ring being able to slide in a fixed ring of said mammography device.

3. A mammography device according to either of claims 1 or 2, wherein the structure has means to move said rings of the structure away from a control cabinet for the mammography device.

4. A mammography device according to claim 3, wherein the structure comprises a bracket, said stirrup being suspended by its top, in a solidly joined way, to a tip of said bracket.

5. A mammography device according to claim 3, wherein the structure comprises a side rest for supporting one of the legs of said stirrup.

6. A mammography device according to either of claims 1 or 2, wherein the structure comprises means for vertical movement.

7. A mammography device according to either of claims 1 or 2, including a supporting plate to keep breasts to be examined under compression, wherein said plate is held, by its side edges, on the two legs of the first ring of the stirrup.

* * * * *